US011331275B2

(12) United States Patent
Liu et al.

(10) Patent No.: US 11,331,275 B2
(45) Date of Patent: May 17, 2022

(54) BEXAROTENE SOFTGEL CAPSULE AND PREPARATION METHOD THEREOF

(71) Applicant: Humanwell PuraCap Pharmaceuticals (Wuhan) Co., Ltd, Wuhan (CN)

(72) Inventors: Bo Liu, Wuhan (CN); Fuxing Shen, Wuhan (CN); Chao Ding, Wuhan (CN); Xiang Ye, Wuhan (CN)

( * ) Notice: Subject to any disclaimer, the term of this patent is extended or adjusted under 35 U.S.C. 154(b) by 0 days.

(21) Appl. No.: 16/139,848

(22) Filed: Sep. 24, 2018

(65) Prior Publication Data

US 2019/0038566 A1 Feb. 7, 2019

Related U.S. Application Data

(63) Continuation of application No. PCT/CN2018/075948, filed on Feb. 9, 2018.

(30) Foreign Application Priority Data

Feb. 16, 2017 (CN) .......................... 201710084373.5

(51) Int. Cl.
| | |
|---|---|
| *A61K 9/48* | (2006.01) |
| *A61K 31/192* | (2006.01) |
| *A61K 47/26* | (2006.01) |
| *A61K 47/02* | (2006.01) |
| *A61K 47/10* | (2017.01) |
| *A61P 35/00* | (2006.01) |

(52) U.S. Cl.
CPC .......... *A61K 9/4833* (2013.01); *A61K 9/4825* (2013.01); *A61K 31/192* (2013.01); *A61K 47/02* (2013.01); *A61K 47/10* (2013.01); *A61K 47/26* (2013.01); *A61P 35/00* (2018.01)

(58) Field of Classification Search
None
See application file for complete search history.

(56) References Cited

U.S. PATENT DOCUMENTS

| 6,217,902 B1 * | 4/2001 | Tanner ................. A61K 9/4833 |
| | | 424/456 |
| 2013/0142871 A1 * | 6/2013 | Paetz ......................... A61J 3/10 |
| | | 424/452 |
| 2014/0235676 A1 * | 8/2014 | Landreth .............. A61K 31/192 |
| | | 514/342 |

FOREIGN PATENT DOCUMENTS

| CN | 102008435 | * | 4/2011 |
| CN | 103181912 A | | 7/2013 |
| JP | H111427 A | | 1/1999 |
| WO | WO-2010065730 A2 * | 6/2010 | ........... A61K 9/0043 |

OTHER PUBLICATIONS

English Machine Translation of CN 103181912 [online], Espacenet [retrieved on Feb. 10, 2020], Retrieved from the internet: <www.epo.org>.*
English Machine Translation of CN 102008435 [online], Espacenet [retrieved on Feb. 10, 2020], Retrieved from the internet: <www.epo.org>.*
Human Translation of Xia et al. (CN 103181912) Provided to the USPTO by Schreiber Translations, Inc. Jun. 2021. (Year: 2021).*
Internation Search Report of PCT/CN2018/075948, dated May 18, 2018.

* cited by examiner

*Primary Examiner* — Katherine Peebles
(74) *Attorney, Agent, or Firm* — W&KIP

(57) ABSTRACT

The present invention discloses a bexarotene softgel capsule and a preparation method thereof. The bexarotene softgel capsule including: a softgel capsule shell and contents, in which the contents include bexarotene, low molecular weight polyethylene glycol, high molecular weight polyethylene glycol, and polysorbate. The bexarotene softgel capsule of the formula can avoid a problem of drug degradation caused by high temperature heat release and degassing difficulty in a process of preparing the bexarotene softgel capsule in the prior art while maintaining the drug release characteristics, and the preparation method has a simple production process and can significantly improve a problem of poor dosage uniformity while filling a capsule in the prior art.

7 Claims, 3 Drawing Sheets

BEXAROTENE SOFTGEL CAPSULE AND PREPARATION METHOD THEREOF

CROSS-REFERENCE TO RELATED APPLICATIONS

This application is a continuation of International Patent Application No. PCT/CN2018/075948 with a filing date of Feb. 9, 2018, designating the United States, now pending, and further claims priority to Chinese Patent Application No. 201710084373.5 with a filing date of Feb. 16, 2017. The content of the aforementioned applications, including any intervening amendments thereto, are incorporated herein by reference.

TECHNICAL FIELD

The present invention belongs to the field of medicine, and in particular, relates to a bexarotene softgel capsule and a preparation method thereof.

BACKGROUND ART

Bexarotene, chemical name: 4-[1-(5,6,7,8-tetrahydro-3,5,5,8,8-pentamethyl-2-naphthyl) ethenyl] benzoic acid; molecular formula: $C_{24}H_{28}O_2$; molecular weight: 348.478; and a chemical structural formula is as follows:

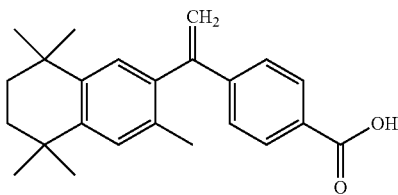 [SMILES: C=C(c1ccc(C(=O)O)cc1)c1cc2c(cc1C)C(C)(C)CCC2(C)C]

The bexarotene is a white to off-white crystalline powder, almost insoluble in water, slightly soluble in methanol, and soluble in acetonitrile and dimethylsulfoxide. The bexarotene has slight hygroscopicity and is used treating refractory and non-refractory cutaneous T cell lymphoma (CTCL). The bexarotene softgel capsule can selectively activate a retinoid X receptor subtype of retinoids (RXRα, RXRβ, RXRγ). RXR can form a heterodimer with a variety of receptors [such as tretinoin receptor (RAR), vitamin D receptor, thyroxine receptor, and peroxisome proliferator-activated receptor (PPAR)]. Once activated, these receptors can control expression of genes and control cell differentiation and proliferation. In an in vitro test, the bexarotene softgel capsule can inhibit growth of certain tumor cell lines; and in an in vivo test of an animal model, the bexarotene softgel capsule can induce mastadenoma to subside.

Once the bexarotene softgel capsule is orally administered, the maximum plasma concentration is reached after about 2 h, and the half-life is about 7 h. Fat-containing food can increase absorption of the bexarotene softgel capsule, and compared with administering glucose solution, administering a fat-containing meal can improve AUC and Cmax of 300 mg of the bexarotene softgel capsule by 35% and 48% respectively. The bexarotene softgel capsule can also be highly combined with plasma protein (>99%).

VALEANT LUXEMBOURG Pharmaceuticals developed a bexarotene softgel capsule (for short, innovator drug, the same below) having a specification of 75 mg. A product manual thereof discloses the bexarotene softgel capsule includes a capsule shell composed of gelatin, glycerol, sorbitol solution, water, and pigment and contents composed of polyethylene glycol 400, povidone, polysorbate 20, butyl hydroxy anisole, and bexarotene. The bexarotene in the formula is suspended in the solution, and the povidone is used as a suspending agent, which can increase viscosity of the formula and maintain uniformity of the drug in the formula. Because bexarotene is an insoluble drug, and the drug formula viscosity is greater than 5,000 cp in the prior art, if the bexarotene is to be dispersed uniformly without agglomeration, mixing time required during production is long, stirring ingredients will release heat and the temperature will reach 80° C. or above, and carboxyl groups in the bexarotene molecule is more easy to react with a large number of hydroxyl groups in the polyethylene glycol 400 molecule; at the same time, because viscosity of the formula is too large, it is difficult to remove oxygen contained in a large number of air bubbles produced during stirring, which will cause degradation of the drug; and because viscosity of the formula is too large, fluidity is poor, which will lead to poor dosage uniformity when filling the capsule.

SUMMARY OF THE INVENTION

The invention aims to solve technical problems in the prior art to some extent, and proposes a bexarotene softgel capsule.

In the present invention, a bexarotene softgel capsule includes: a softgel capsule shell and contents, in which the contents include bexarotene, low molecular weight polyethylene glycol, high molecular weight polyethylene glycol, and polysorbate.

In addition, the bexarotene softgel capsule of the present invention may also have the following additional technical features:

In the invention, the low molecular weight polyethylene glycol may have a molecular weight of 200~600, for example, 400.

In the invention, the high molecular weight polyethylene glycol may have a molecular weight of 1,000~4,000, for example, 2,000.

In the invention, the polysorbate may be selected from one or more of polysorbate 20, polysorbate 40, and polysorbate 60, for example, polysorbate 20.

Therefore, drug properties of the bexarotene softgel capsule can be further ensured.

In the invention, the bexarotene may have a particle diameter D90 of less than 20 μm.

In the invention, a weight ratio of the bexarotene, low molecular weight polyethylene glycol, high molecular weight polyethylene glycol, and polysorbate may be 1:4~8:0.5~1.5:0.6~1.0, for example, 1:6:1:0.8.

The invention also provides a preparation method of the bexarotene softgel capsule, which includes:

(1) mixing and heating bexarotene, low molecular weight polyethylene glycol, high molecular weight polyethylene glycol, and polysorbate to obtain a mixed liquid drug; and (2) pressing a sol and the mixed liquid drug obtained in step (1) on a softgel capsule machine to perform pressing, to obtain the bexarotene softgel capsule.

In addition, the preparation method of the bexarotene softgel capsule of the present invention may also have the following additional technical features:

In the invention, the sol is a solution containing starch or a sol composed of gelatin, glycerol, sorbitol, water, and titanium dioxide.

In the invention, the step (1) may be performed according to the following steps:

S1: mixing and heating the high molecular weight polyethylene glycol, polysorbate, and low molecular weight polyethylene glycol to obtain a mixed melt; and S2: cooling the mixed melt and then mixing the mixed melt with the bexarotene to obtain a mixed liquid drug, and insulating the mixed liquid drug at 30~35° C.

In the invention, in the step S1, the mixing and heating includes heating the low molecular weight polyethylene glycol to 60~80° C., and then adding the high molecular weight polyethylene glycol and polysorbate thereto, maintaining the temperature at 60~80° C., and stirring to dissolve, to obtain the mixed melt.

In the invention, in the step S2, temperature of the cooled mixed melt may be 355~45° C.

Compared with the prior art, the bexarotene softgel capsule produced by the formula can avoid a problem of drug degradation caused by high temperature heat release and degassing difficulty in a process of preparing the bexarotene softgel capsule in the prior art while maintaining the drug release characteristics, and the preparation method has a simple production process and can significantly improve a problem of poor dosage uniformity while filling a capsule in the prior art.

DETAILED DESCRIPTION OF THE INVENTION

Figure 1:
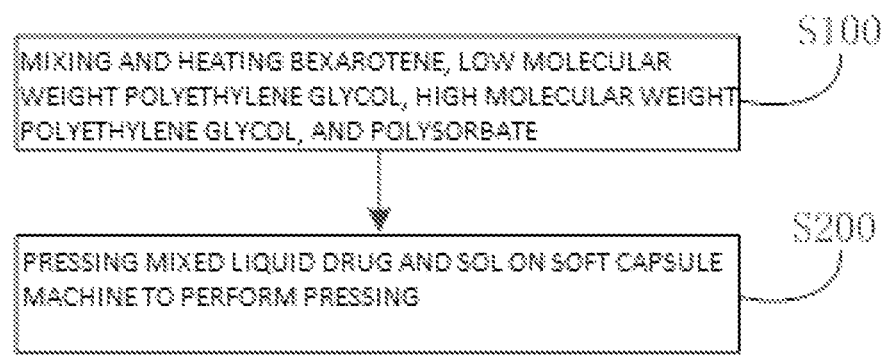
FIG. 1 is a flow diagram of a method of preparing a bexarotene softgel capsule according to an embodiment of the present invention.

In order to make the object, technical solution, and advantages of the present invention more clear, the present invention is further described in detail below in connection with drawings and embodiments. Additional aspects and advantages of the invention will be given in part in the following description, and a part will be obvious from the following description or learned by practice of the invention. It should be understood that the following description is merely illustrative of the invention and is not intended to limit the invention. Furthermore, description of terms "an embodiment", "some embodiments", "example", "particular example", "some examples", or the like that are described below means that a particular feature, structure, material, or characteristic described in connection with the embodiment or example is included in at least one embodiment or example of the invention. In this specification, schematic representations of the above terms are not necessarily for the same embodiment or example. Furthermore, technical features involved in each embodiment of the present invention may be combined with each other as long as they do not conflict with each other.

The present invention provides a bexarotene softgel capsule, and according to embodiments of the invention, the bexarotene softgel capsule includes: a softgel capsule shell and contents, in which the contents include bexarotene, low molecular weight polyethylene glycol, high molecular weight polyethylene glycol, and polysorbate. The inventor found that the bexarotene softgel capsule of the composition can avoid a problem of drug degradation caused by high temperature heat release and degassing difficulty in a process of preparing the bexarotene softgel capsule in the prior art while maintaining the drug release characteristics.

According to an embodiment of the invention, the molecular weight of the low molecular weight polyethylene glycol in the invention is not particularly limited, a person skilled in the art may choose according to actual needs, and according to a particular embodiment of the invention, the low molecular weight polyethylene glycol may have a molecular weight of 200~600, for example, 400. The inventor found that the low molecular weight polyethylene glycol must be liquid as a main substrate at room temperature and during processing. Polyethylene glycol whose molecular weight is too high (higher than 600) is solid, cannot fill a softgel capsule, and is adverse to product dissolution, and polyethylene glycol whose molecular weight is lower than 200 cannot be used as a pharmaceutical excipient.

According to another embodiment of the invention, the molecular weight of the high molecular weight polyethylene glycol in the invention is not particularly limited, a person skilled in the art may choose according to actual needs, and according to a particular embodiment of the invention, the high molecular weight polyethylene glycol may have a molecular weight of 1,000~4,000, for example, 2,000. The inventor found that the high molecular weight polyethylene glycol having a molecular weight of 1,000~4,000 is used as a suspending agent with the low molecular weight polyethylene glycol in a certain proportion in the formula may form mixed systems having different melting points, that is, the higher the molecular weight or a proportion of use of the high molecular weight polyethylene glycol is, the higher the melting point of the system is, the greater the viscosity is, and the stronger the suspension effect is, but when the melting point of the system is higher than 40° C., the softgel capsule cannot be filled.

According to another embodiment of the invention, a particular type of polysorbate in the invention is not particularly limited, a person skilled in the art may choose according to actual needs, and according to a particular embodiment of the invention, polysorbate may be selected from one or more of polysorbate 20, polysorbate 40, and polysorbate 60, for example, polysorbate 20. The inventor found that HLB values and hydrophilicities of polysorbate 60, polysorbate 40, and polysorbate 20 (hydrophilic oleophilic balance value) increase in sequence. The polyethylene glycol used in the formula is a hydrophilic excipient, and polysorbate 60, polysorbate 40, and polysorbate 20 have substantially the same solubilization ability for drugs, so polysorbate 20 having the largest HLB value is preferable in the formula.

According to another embodiment of the invention, the particle size of the bexarotene in the invention is not particularly limited, a person skilled in the art may choose according to actual needs, and according to a particular embodiment of the invention, the bexarotene may have a particle diameter D90 of less than 20 am. The inventor found that the bexarotene is an insoluble drug, but an in vivo permeability thereof is good, the drug dissolved in vivo will immediately be absorbed, the larger the particle size is, the more slowly the drug dissolves; the smaller the particle size is, the faster the drug dissolves.

According to another embodiment of the invention, a weight ratio of bexarotene, low molecular weight polyethylene glycol, high molecular weight polyethylene glycol, and polysorbate in the invention is not particularly limited, a person skilled in the art may choose according to actual needs, and according to a particular embodiment of the invention, the weight ratio of bexarotene, low molecular weight polyethylene glycol, high molecular weight polyethylene glycol, and polysorbate may be 1:4~8:0.5~1.5: 0.6~1.0, for example, 1:6:1:0.8. The inventor found that according to the dosage and particle size of the drug materials, if the high molecular weight polyethylene glycol is too much with respect to the low molecular weight polyethylene glycol, the melting point and viscosity of the system will be relatively high, and the capsule cannot be filled; if the high molecular weight polyethylene glycol is too little with respect to the low molecular weight polyethylene glycol, the melting point and viscosity of the system will be relatively low, the drugs cannot be dispersed stably and uniformly in the system.

According to another embodiment of the present invention, a particular type of the softgel capsule shell is not particularly limited, a person skilled in the art may choose according to actual needs. In particular, the sol is a solution containing starch or a sol composed of gelatin, glycerol, sorbitol, water, and titanium dioxide.

A large number of experiments by the inventor prove that the bexarotene softgel capsule produced according to the formula of the present invention can avoid a problem of drug degradation caused by high temperature heat release and degassing difficulty in a process of preparing the bexarotene softgel capsule in the prior art while maintaining the drug release characteristics.

The invention also provides a method of preparing the bexarotene softgel capsule, according to embodiments of the invention and referring to FIG. 1, which includes:

S100: mixing and heating bexarotene, low molecular weight polyethylene glycol, high molecular weight polyethylene glycol, and polysorbate to obtain a mixed liquid drug.

Figure 2:
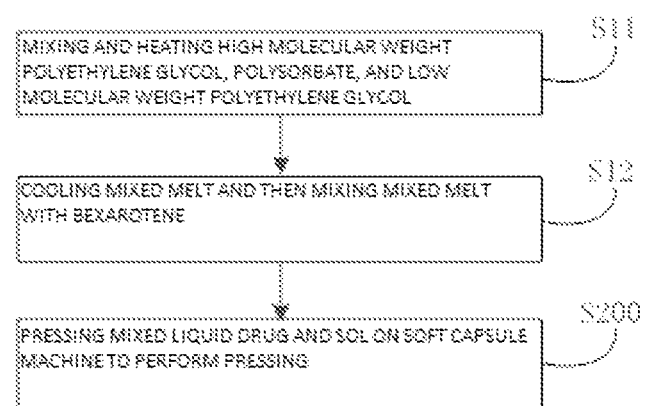
FIG. 2 is a flow diagram of a method of preparing a bexarotene softgel capsule according to another embodiment of the present invention.

In particular, according to an embodiment of the invention and referring to FIG. 2, the S100 is performed according to the following steps:

S11: mixing and heating the high molecular weight polyethylene glycol, polysorbate, and low molecular weight polyethylene glycol.

In this step, mixing and heating the high molecular weight polyethylene glycol, polysorbate, and low molecular weight polyethylene glycol to obtain a mixed melt. In particular, heating the low molecular weight polyethylene glycol to 60~80° C., and then adding the high molecular weight polyethylene glycol and polysorbate thereto, mixing and heating, maintaining the temperature at 60~80° C., and stirring to dissolve. While being heated, the high molecular weight polyethylene glycol completely melts and dissolves in the low molecular weight polyethylene glycol to form a semisolid paste at room temperature.

According to a particular embodiment of the present invention, mixing and heating temperature is 60~80° C. The inventor found that the mixing and heating temperature is 60~80° C. and can ensure that the high molecular weight polyethylene glycol completely melts and dissolves, and when the temperature is too low, the dissolution is slow; when the temperature is too high, polyethylene glycol will degrade.

S12: cooling the mixed melt and then mixing the mixed melt with the bexarotene.

In this step, cooling the mixed melt and then mixing the mixed melt with the bexarotene to obtain a mixed liquid drug. In particular, cooling the mixed melt to 40~45° C. after the dissolution, and then adding the bexarotene thereto, and stirring uniformly. Thus, mixing time can be reduced, and because the bexarotene is added when mixed melt liquid of the low molecular weight polyethylene glycol, high molecular weight polyethylene glycol, and polysorbate is cooled to 40~45° C., which can avoid chemical reactions between carboxyl groups in the bexarotene and hydroxyl groups in the mixed melt, can avoid stirring to produce a large number of bubbles, and can avoid a problem of drug degradation caused by high temperature heat release and degassing difficulty.

According to a particular embodiment of the invention, temperature of the cooled mixed melt is 40~45° C. The inventor found that when the temperature of the mixed melt is too low, the viscosity of the mixed melt will increase, the mixed melt is not easy to stir uniformly, and degassing is difficult; when the temperature is too high, the carboxyl groups in the bexarotene will react with the hydroxyl groups in the mixed melt liquid.

S200: pressing a sol and the mixed liquid drug on a softgel capsule machine to perform pressing.

In this step, pressing a sol and the mixed liquid drug on a softgel capsule machine to perform pressing, to obtain the bexarotene softgel capsule. In particular, insulating the mixed liquid drug at 30~35° C., then pressing the mixed liquid drug with the sol on the softgel capsule machine, and drying, polishing and packing to obtain the bexarotene softgel capsule. The invention found that the method of preparing the bexarotene softgel capsule by using embodiments of the invention can significantly improve a problem of poor dosage uniformity when filling a capsule in the prior art. In particular, the sol may be a solution containing starch or a sol composed of gelatin, glycerol, sorbitol, water, and titanium dioxide.

The present invention will be described below with reference to particular Examples.

Example 1

(1) Content composition: 75 g of bexarotene (D90 is less than 20 μm), 450 g of polyetheylene glycol 400, 75 g of polyetheylene glycol 2000, and 60 g of polysorbate 20.

(2) Preparation method: first heating polyethylene glycol 400 to 60~80° C., and then adding polyethylene glycol 2000 and polysorbate 20 thereto, maintaining the temperature of 60~80° C., stirring, cooling to 40~45° C. after dissolution, and then adding bexarotene thereto and stirring uniformly, to obtain a mixed liquid drug. Next insulating the mixed liquid drug at 30~35° C., then pressing the mixed liquid drug with a sol (composed of gelatin, glycerol, sorbitol, water, and titanium dioxide) on a softgel capsule machine, and drying, polishing and packing to obtain a bexarotene softgel capsule. Production process data thereof are shown in Table 1.

Example 2

(1) Content composition: 75 g of bexarotene (D90 is less than 20 m), 600 g of polyetheylene glycol 600, 75 g of polyetheylene glycol 1000, and 45 g of polysorbate 40.

(2) Preparation method: first heating polyethylene glycol 600 to 60~80° C., and then adding polyethylene glycol 1000 and polysorbate 40 thereto, maintaining the temperature of 60~80° C., stirring, cooling to 40~45° C. after dissolution, and then adding bexarotene thereto and stirring uniformly. Insulating the mixed liquid drug at 30~35° C., then pressing the mixed liquid drug with a sol (composed of gelatin, glycerol, sorbitol, water, and titanium dioxide) on a softgel capsule machine, and drying, polishing and packing to obtain a bexarotene softgel capsule. Production process data thereof are shown in Table 1.

Example 3

(1) Content composition: 75 g of bexarotene (D90 is less than 20 μm), 300 g of polyetheylene glycol 400, 37.5 g of polyetheylene glycol 1000, and 75 g of polysorbate 40.

(2) Preparation method: first heating polyethylene glycol 400 to 6080° C., and then adding polyethylene glycol 1000 and polysorbate 40 thereto, maintaining the temperature of 60~80° C., stirring, cooling to 40~45° C. after dissolution, and then adding bexarotene thereto and stirring uniformly. Insulating the mixed liquid drug at 3035° C., then pressing the mixed liquid drug with a sol (composed of gelatin, glycerol, sorbitol, water, and titanium dioxide) on a softgel capsule machine, and drying, polishing and packing to obtain a bexarotene softgel capsule. Production process data thereof are shown in Table 1.

Example 4

(1) Content composition: 75 g of bexarotene (D90 is less than 20 μm), 450 g of polyetheylene glycol 200, 37.5 g of polyetheylene glycol 2000, and 75 g of polysorbate 60.

(2) Preparation method: first heating polyethylene glycol 200 to 60~80° C., and then adding polyethylene glycol 2000 and polysorbate 60 thereto, maintaining the temperature of 60~80° C., stirring, cooling to 40~45° C. after dissolution, and then adding bexarotene thereto and stirring uniformly. Insulating the mixed liquid drug at 30~35° C., then pressing the mixed liquid drug with a sol (composed of gelatin, glycerol, sorbitol, water, and titanium dioxide) on a softgel capsule machine, and drying, polishing and packing to obtain a bexarotene softgel capsule. Production process data thereof are shown in Table 1.

Example 5

(1) Content composition: 75 g of bexarotene (D90 is less than 20 jam), 600 g of polyetheylene glycol 200, 37.5 g of polyetheylene glycol 4000, and 60 g of polysorbate 20.

Figure 3:
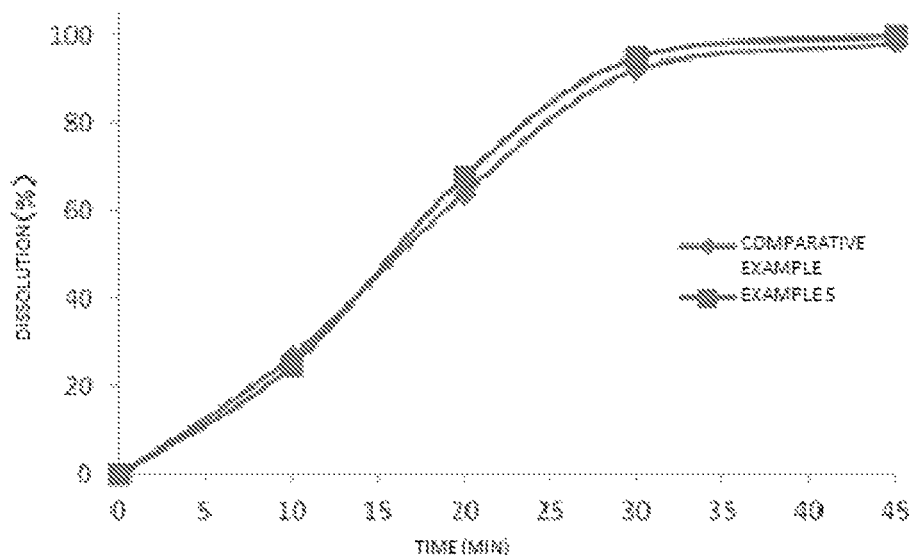
FIG. 3 is a dissolution curve comparison chart of bexarotene softgel capsules obtained in Example 5 and Comparative Example.

(2) Preparation method: first heating polyethylene glycol 200 to 60~80° C., and then adding polyethylene glycol 4000 and polysorbate 20 thereto, maintaining the temperature of 60~80° C., stirring, cooling to 40~45° C. after dissolution, and then adding bexarotene thereto and stirring uniformly. Insulating the mixed liquid drug at 30~35° C., then pressing the mixed liquid drug with a sol (composed of gelatin, glycerol, sorbitol, water, and titanium dioxide) on a softgel capsule machine, and drying, polishing and packing to obtain a bexarotene softgel capsule. Production process data thereof are shown in Table 1, and a dissolution curve thereof is shown in FIG. 3.

Comparative Example

A formula of a control drug bexarotene softgel capsule is 75 g of bexarotene, 650 g of polyethylene glycol 400, 30 g of polysorbate 20, and 40 g of povidone;

Preparation method: heating the polyethylene glycol to about 50° C., adding polysorbate 20 and povidone, stirring to dissolve, adding the bexarotene, stirring uniformly at a rotational speed of 2,000 rpm to 3,000 rpm, then pressing the mixed liquid drug with a sol (composed of gelatin, glycerol, sorbitol, water, and titanium dioxide) on a softgel capsule machine, and drying, polishing and packing to obtain a bexarotene softgel capsule. Production process data thereof are shown in Table 1.

TABLE 1

Production process data of Examples 1-5 and Comparative Example

|  | Example 1 | Example 2 | Example 3 | Example 4 | Example 5 | Comparative Example |
| --- | --- | --- | --- | --- | --- | --- |
| Drug mixing and stirring speed | 300 rpm to 500 rpm | 300 rpm to 500 rpm | 300 rpm to 500 rpm | 300 rpm to 500 rpm | 300 rpm to 500 rpm | 2,000 rpm to 3,000 rpm |
| Time for mixing and uniformly stirring drug | At least 20 minutes | At least 20 minutes | At least 20 minutes | At least 20 minutes | At least 20 minutes | At least 40 minutes |
| Maximum temperature during stirring | At most 45° C. | At most 45° C. | At most 45° C. | At most 45° C. | At most 45° C. | 82° C. |
| Degassing time | Degassing for 15 to 30 minutes under −0.06 MPa to 0.09 MPa | Degassing for 15 to 30 minutes under −0.06 MPa to 0.09 MPa | Degassing for 15 to 30 minutes under −0.06 MPa to 0.09 MPa | Degassing for 15 to 30 minutes under −0.06 MPa to 0.09 MPa | Degassing for 15 to 30 minutes under −0.06 MPa to 0.09 MPa | Difficult to degas, and needs vacuum standing for at least 12 hours. |
| Ingredient uniformity (upper, medium, and lower sampling) | 0.8% | 0.8% | 0.8% | 0.8% | 0.8% | RSD 2.5% |
| Polyethylene glycol ester impurity | Not detected | Not detected | Not detected | Not detected | Not detected | 0.12% |

A person skilled in the art will readily understand that the above-described embodiments are merely exemplary and are not intended to limit the present invention, and any modifications, equivalent substitutions, improvements, and the like made within the spirit and principles of the invention shall be included in the scope of claims of the invention.

We claim:

1. A bexarotene softgel capsule comprising: a softgel capsule shell and contents, wherein the contents consist essentially of bexarotene, low molecular weight polyethylene glycol with a molecular weight of 200 to 600, high molecular weight polyethylene glycol with a molecular weight of 1,000 to 2,000, and polysorbate, wherein the weight ratio of the bexarotene, low molecular weight polyethylene glycol, high molecular weight polyethylene glycol, and polysorbate is 1:4-8:0.5-1.5:0.6-1.0.

2. The bexarotene softgel capsule according to claim 1, wherein the polysorbate is selected from one or more of polysorbate 20, polysorbate 40, and polysorbate 60.

3. The bexarotene softgel capsule according to claim 1, wherein the bexarotene is in particulate form and has a particle size D90 of less than 20 µm.

4. A preparation method of the bexarotene softgel capsule according to any one of claim 1, comprising the following steps:
(1) mixing and heating bexarotene, low molecular weight polyethylene glycol with a molecular weight of 200 to 600, high molecular weight polyethylene glycol with a molecular weight of 1,000 to 2,000, and polysorbate to obtain a mixed liquid drug, wherein the weight ratio of the bexarotene, low molecular weight polyethylene glycol, high molecular weight polyethylene glycol, and polysorbate is 1:4-8:0.5-1.5:0.6-1.0; and
(2) pressing a sol and the mixed liquid drug obtained in step (1) on a softgel capsule machine to perform pressing, to obtain the bexarotene softgel capsule.

5. The preparation method of the bexarotene softgel capsule according to claim 4, wherein the step (1) is performed according to the following steps:
S1: mixing and heating the high molecular weight polyethylene glycol, polysorbate, and low molecular weight polyethylene glycol to obtain a mixed melt; and
S2: cooling the mixed melt and then mixing the mixed melt with the bexarotene to obtain a mixed liquid drug, and insulating the mixed liquid drug at 30-35° C.

6. The preparation method of the bexarotene softgel capsule according to claim 4, wherein the sol in the step (2) is a solution containing starch or a sol composed of gelatin, glycerol, sorbitol, water, and titanium dioxide.

7. The preparation method of the bexarotene softgel capsule according to claim 5, wherein, in the step S1, the mixing and heating includes heating the low molecular weight polyethylene glycol to 60-80° C., then adding the high molecular weight polyethylene glycol and polysorbate thereto, maintaining the temperature at 60-80° C., and stirring to dissolve, to obtain the mixed melt.

* * * * *